(12) United States Patent
Ashwood Smith

(10) Patent No.: US 6,738,354 B1
(45) Date of Patent: May 18, 2004

(54) LABEL SELECTION FOR END-TO-END LABEL-SWITCHED TRAFFIC THROUGH A COMMUNICATIONS NETWORK

(75) Inventor: Peter J. Ashwood Smith, Hull (CA)

(73) Assignee: Nortel Networks Limited (CA)

( * ) Notice: Subject to any disclaimer, the term of this patent is extended or adjusted under 35 U.S.C. 154(b) by 0 days.

(21) Appl. No.: 09/507,080

(22) Filed: Feb. 18, 2000

(51) Int. Cl.[7] .............................. H04J 4/00; H04L 12/24
(52) U.S. Cl. ...................... 370/248; 370/352; 370/389; 370/409
(58) Field of Search ................................ 370/351, 389, 370/392, 393, 395.1, 396, 397, 395.2, 395.3, 395.31, 395.5, 395.51, 395.52, 395.54, 400, 409, 410

(56) References Cited

U.S. PATENT DOCUMENTS

| | | | |
|---|---|---|---|
| 4,577,311 A | | 3/1986 | Duquesneé et al. ............ 370/60 |
| 4,736,363 A | | 4/1988 | Aubin et al. .................... 370/60 |
| 4,995,032 A | | 2/1991 | Demichelis et al. ........... 370/60 |
| 5,229,988 A | * | 7/1993 | Marbaker et al. ............. 370/245 |
| 5,367,517 A | * | 11/1994 | Cidon et al. ................... 370/431 |
| 5,579,480 A | | 11/1996 | Cidon et al. .................. 395/200.1 |
| 5,781,537 A | * | 7/1998 | Ramaswami et al. ........ 370/254 |
| 5,996,021 A | | 11/1999 | Civanlar et al. .............. 709/238 |
| 6,175,870 B1 | * | 1/2001 | Gawlick et al. ............... 709/227 |
| 6,339,595 B1 | * | 1/2002 | Rekhter et al. ............... 370/392 |
| 6,418,126 B1 | * | 7/2002 | Gilmurray et al. ........... 370/310.1 |

* cited by examiner

*Primary Examiner*—Huy D. Vu
*Assistant Examiner*—Daniel Ryman
(74) *Attorney, Agent, or Firm*—Steubing McGuinness & Manaras LLP

(57) ABSTRACT

In a method of label selection for end-to-end transport of label switched traffic through a communications network between a source node and a destination node, a request message is launched toward the destination node from the source node. The request message includes a label list having one or more label identifiers indicative of respective corresponding labels available for use by the source node. The label list is revised, at a cross-connect service each successive hop between the source node and the destination node, based on labels available for use by each respective hop, to produce a reduced label list. The reduced label list includes label identifiers indicative of respective corresponding labels available for end-to-end transport of label switched traffic between the source node and the destination node.

24 Claims, 3 Drawing Sheets

LABEL SELECTION FOR END-TO-END LABEL-SWITCHED TRAFFIC THROUGH A COMMUNICATIONS NETWORK

CROSS-REFERENCE TO RELATED APPLICATIONS.

This is the first application filed for the present invention.

MICROFICHE APPENDIX

Not Applicable.

TECHNICAL FIELD

The present invention relates to mapping communications paths through a communications network, and in particular to label selection for end-to-end label switched traffic through a communications network.

BACKGROUND OF THE INVENTION

Optical communications networks have recently become established, as the preferred backbone for data communications because of the high bandwidth capacity of the optical fiber links. In the modern network space, packetized data traffic of multiple different protocols (e.g. internet protocol, frame relay, asynchronous transfer mode, etc.) is transported over a common network infrastructure. Each protocol provides its own packet (or frame) size and format standards. Additionally, some protocols (e.g. IP) are specifically designed to allow packets having widely varying lengths. New routing protocols, for example the multi-protocol label switching (MPLS) protocol have been proposed to facilitate multi-protocol traffic across a common network infrastructure.

Under the MPLS protocol, label switched packets (LSPs) are propagated across the network hop-by-hop along a path that is set up at the beginning of a communications session. In general, the label assigned to the LSP can be different for each hop, with the label conversion being performed by the node serving the respective hop. Where the network is designed for wave division multiplex (WDM) transport of data traffic, it is desirable to use a data channel (or wavelength) as the label assign to an LSP through a respective hop. In this case, end-to-end transport of an LSP through an MPLS path requires a change of wavelength in the node serving each hop.

However, the, modern network space is composed of a mixture of agile cross-connects (i.e. cross-connects capable of wavelength conversion from input to output) and non agile cross-connects (i.e. cross-connects that are unable to do wavelength conversion). Because MPLS normally requires that the labels (i.e. the wavelengths) must be changeable at every hop, non agile cross-connects within the network cannot participate in an MPLS end-to-end optical path. This restriction forces MPLS traffic to be routed around non-agile cross-connects, and serves as a barrier to the widespread implementation of MPLS.

A technique which allows non-ageile cross-connects to participate in MPLS end-to-end optical paths is therefore highly desirable.

SUMMARY OF THE INTENTION

An object of the present invention is to provide a technique which enables an MPLS end-to-end optical path to be mapped through a communications network, in which at least one and possibly all of the nodes participating in the path are non-agile.

A further object of the present invention is to provide a technique enabling an MPLS end-to-end optical path to be mapped across a communications network using a common label (e.g. wavelength) for every hop of the path, so that inter-hop label conversion is not necessary.

Accordingly, an aspect of the present invention provides a method of label selection for end-to-end transport of label switched traffic through a communications network between a source node and a destination node. A request message is launched toward the destination node from the source node. The request message includes a label list having one or more label identifiers indicative of respective corresponding labels available for use by the source node. The label list is revised, at a cross-connect service each successive hop between the source node and the destination node, based on labels available for use by each respective hop, to produce a reduced label list. The reduced label list includes label identifiers indicative of respective corresponding labels available for end-to-end transport of label switched traffic between the source node and the destination node.

A further aspect of the present invention provides communications network adapted for end-to-end transport of label switched traffic through the communications network.

The communications network comprises a source node, a destination node, and at least one cross-connect intermediate the source node and the destination node. The source node is adapted to launch a request message toward a destination node. The request message includes a label list having one or more label identifiers indicative of respective corresponding labels available for use by the source node. Each cross-connect is adapted to revise the label list based on labels available for use over a successive hop served by the cross-connect, to produce a reduced label list.

A still further aspect of the invention provides a cross-connect of a communications network adapted for end-to-end transport of label switched traffic through the communications network between a source node and a destination node. The cross-connect includes a label availability table, a buffer and a processor. The label availability table includes label identifiers indicative of labels available for a successive hop served by the cross-connect. The buffer is adapted to receive a request message propagated through the communications network from the source node. The request message includes a label list having label identifiers indicative of labels available for conveying label switched traffic between the source node and the cross-connect. The processor is adapted to revise the label list included in the received request message, based on the label availability table, to produce a reduced label list.

The communications network may be adapted for wave division multiplex (WDM) transport of label switched traffic, each label comprising a respective data transport wavelength.

The label switched traffic may include multi-protocol label switched (MPLS) traffic.

In an embodiment of the invention, the step of revising the label list comprises, at each cross-connect serving a successive, hop toward the destination node, a step of intersecting the label list with a set of label identifiers indicative of labels available for use over the hop. A request rejection message may be sent to the source node if the reduced label list is empty.

If the reduced label list included with the request message received by the destination node contains at least one label identifier, then one of the label identifiers is selected from the reduced label list. An end-to-end label switched path is then set up between the source node and the destination node using the respective label corresponding to the selected label identifier. The label identifier may be selected at random from the reduced label list.

The step of setting up an end-to-end label switched path may include sending a mapping message containing the selected label identifier from the destination node toward the source node, the mapping message retracing the path traversed by the request message. Upon receipt of the mapping message at the cross-connect serving each hop, the corresponding label indicated by the, selected label identifier is assigned to the end-to-end label switched path, if the label is still available for use by the hop.

A mapping failure message may be sent to the destination node if the label corresponding to the selected label identifier is not available for use by the hop. In this case, upon receipt of the mapping failure message by the destination node, the reduced label list may be stripped by removing the selected label identifier. If the thereby stripped label list is empty, a request rejection message may then be sent to the source node. Otherwise, if the stripped label list contains at least one label identifier, a new label identifier may be selected from the stripped label list, and an end-to-end label switched path set up between the source node and the destination node using the respective label corresponding to the newly selected label identifier.

BRIEF DESCRIPTION OF THE DRAWINGS

Further features and advantages of the present invention will become apparent from the following detailed description, taken in combination with the appended drawings, in which.

It will be :noted that throughout the appended drawings, like features are identified by like reference numerals.

DETAILED DESCRIPTION OF THE PREFERRED EMBODIMENT

Figure 1:
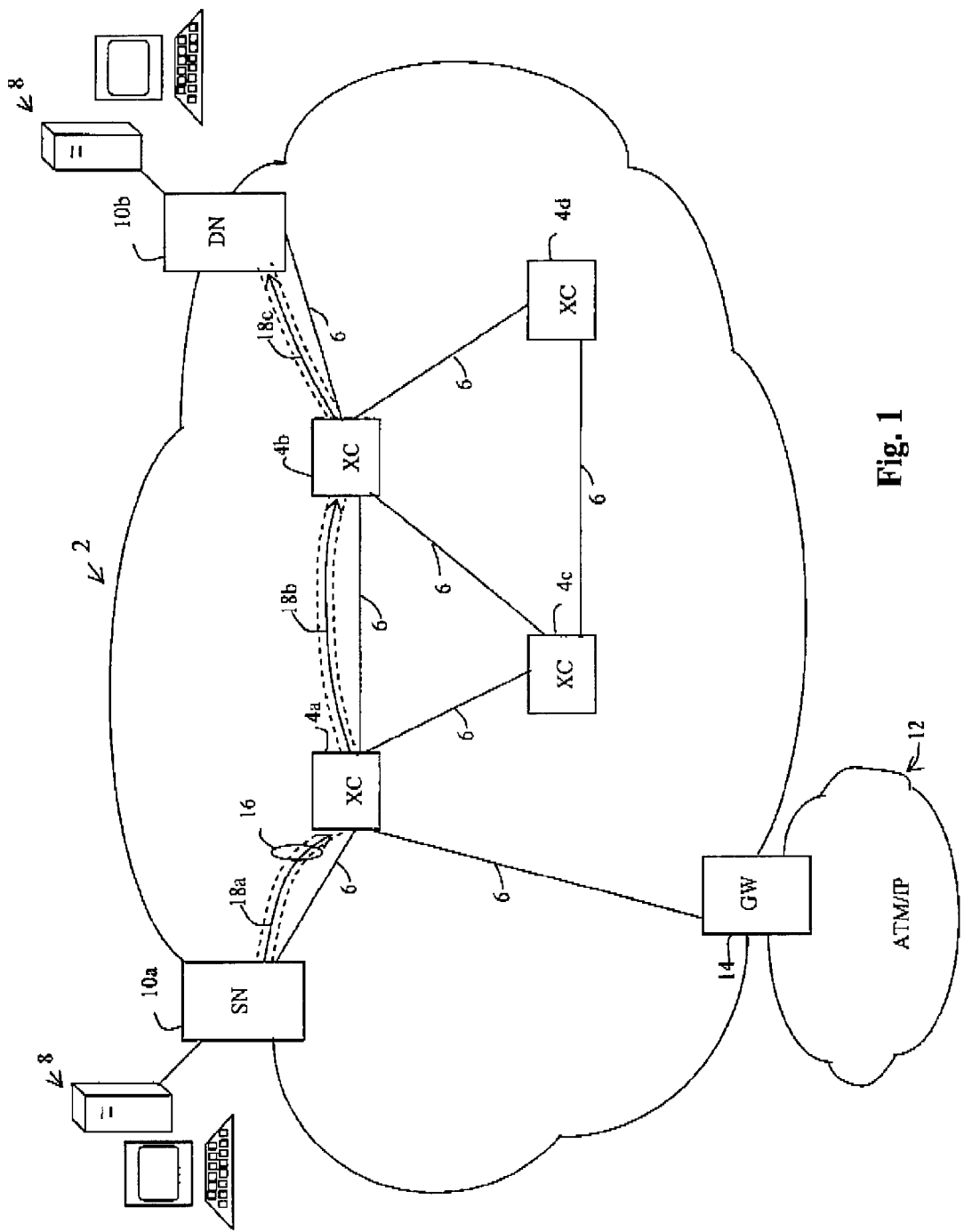
FIG. 1 is a block diagram illustrating an optical communications network usable in conjunction with an embodiment of the present invention.

As shown in FIG. 1, an optical network 2 usable in conjunction with the present invention generally comprises a plurality of cross-connects 4 (four are shown in FIG. 1) interconnected by fiber optic links 6. Communications devices 8, for example end user personal computers (PCs) or local area network (LAN) servers may be connected to the optical network 2 via one or more edge nodes (or access points) 10. The optical network 2 may also be connected to one or more federated networks 12, for example an asynchronous transfer mode (ATM) or an internet protocol (IP) network, through a respective gateway 14. Within the optical network 2, each of the cross-connects 4 is configured for wave division multiplex (WDM) and/or dense wave division multiplex (DWDM) transport of packet data traffic as will be described in greater detail below.

The present invention provides a technique for label selection for an MPLS end-to-end optical path 16 across the communications network 2 between a source node 10a and a destination node 10b via one or more intervening cross connects 4. The path 16 is divided into hops 18, each of which is served by a respective node (e.g., the source node 10a of a cross-connect 4) connected at the up-stream end of the hop 18. In a WDM (or DWDM) environment, the label assigned to each label switched packet (LSP), for each hop 18, is the channel (wavelength) used for conveying the LSP through the hop. In other words, the label designates the wavelength on which the path 16 traverses the hop 18. In the example illustrated in FIGS. 1 and 3, the source and destination nodes 10a and 10b are located at respective edge nodes, and two intervening cross-connects 4a and 4b are incorporated into the path 16. One or both of the cross connects 4a, b may be non-agile, so that label (thus wavelength) conversion between hops (i.e. within a cross-connect 4) may not be possible. Thus in accordance with the present invention, a common label is selected such that the label switched end-to-end optical path 16 using the common label (wavelength) can be mapped across the communications network 2.

Figure 2:
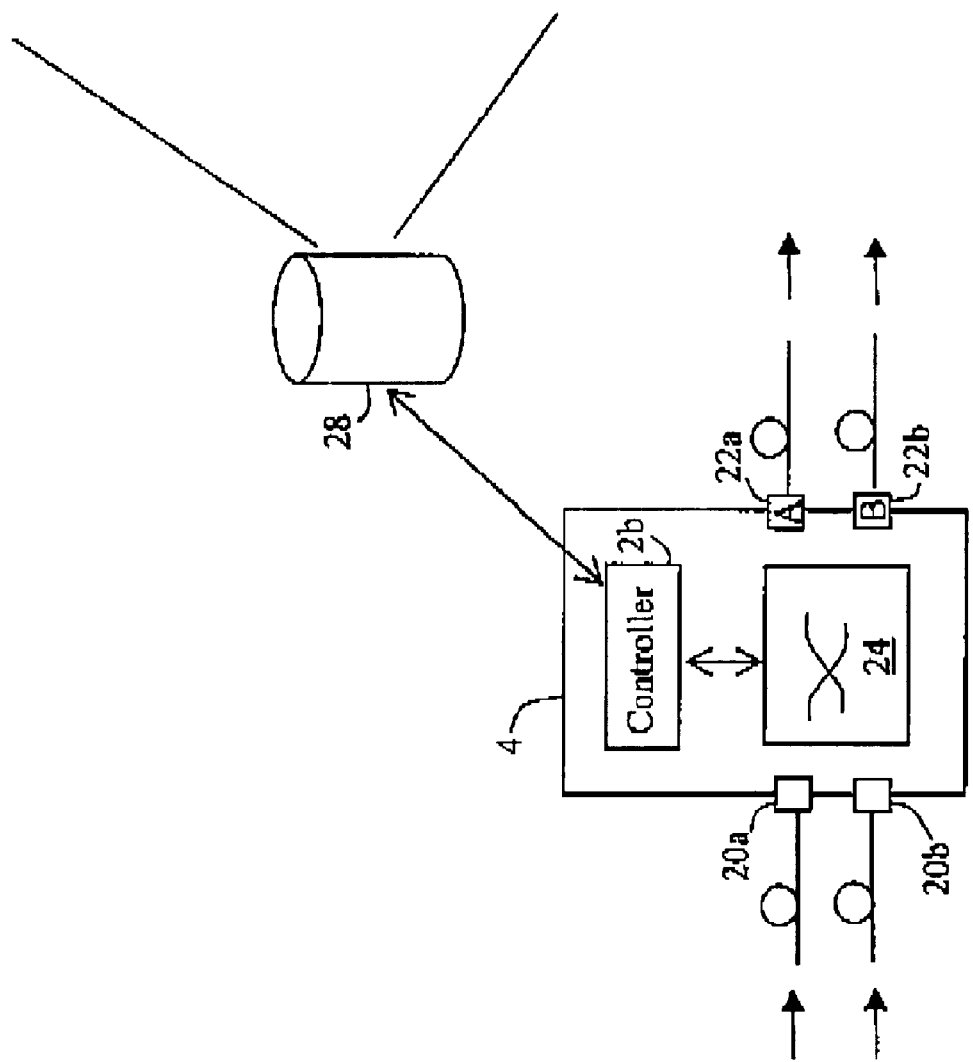
FIG. 2 is a block diagram schematically illustrating principal elements of a cross-connect usable in the optical communications network illustrated in FIG. 1.

FIG. 2 is a block diagram schematically illustrating the principal elements of a cross-connect 4 of the optical network. As shown in FIG. 2, the cross-connect 4 includes at least one input port 20; at least one output port 22; a switch 24 (which may be an optical space switch) capable of providing a signal path between respective input and output ports 20, 22; a controller 26 for controlling operation of the cross-connect 4; and a label availability table 28, which may be co-resident with the cross-connect 4 or located at a remote site and accessible by the controller 26. The controller 26 can be provided with a buffer (not shown) for temporarily storing information.

In the embodiment of FIG. 2 the cross-connect 4 is provided with two input ports 20a and 20b and two output ports 22a and 22b. However, it will be, appreciated that a greater or smaller number of ports may be provided in the cross-connect 4, and/or the cross-connect 4 may be provided with a plurality of ports of which one or more may remain unused. It will also be appreciated that the ports of the cross-connect 4 may be suitably designed and connected to handle bi-directional data traffic. However, in order to simplify the present description, and aid understanding of the invention, the, embodiment of FIG. 2 is provided with unidirectional ports, two of which (input ports 20a and 20b) are connected to handle inbound LSPs, and the other two (output ports 22a and 22b) are connected to handle outbound LSPs.

The label availability table 28 dynamically stores information concerning the availability of each label which can be used for transporting LSPs over hops 18 immediately downstream of the cross-connect 4. Thus for each output port 22, the label availability table 28 contains a list of label identifiers corresponding to each label (i.e. transmission wavelength), and an associated availability flag. The availability flag may conveniently be a binary value, in which a "1" indicates that the respective label indicated by the corresponding label identifier is available for use, and a "0" indicates that the respective label is not available for use. The label availability table 28 can be dynamically maintained by updating the availability flag as label switched paths 16 are set up and released. In the embodiment illustrated in FIGS. 2 and 3, four labels (indicated by respective label identifiers $\lambda_1$ through $\lambda_4$) may by used for label switched traffic. Clearly, more, or fewer labels may be used, as desired;

Operation of the cross connect 4, and the method of the present invention, is described in greater detail below with reference to FIG. 3.

Figure 3:
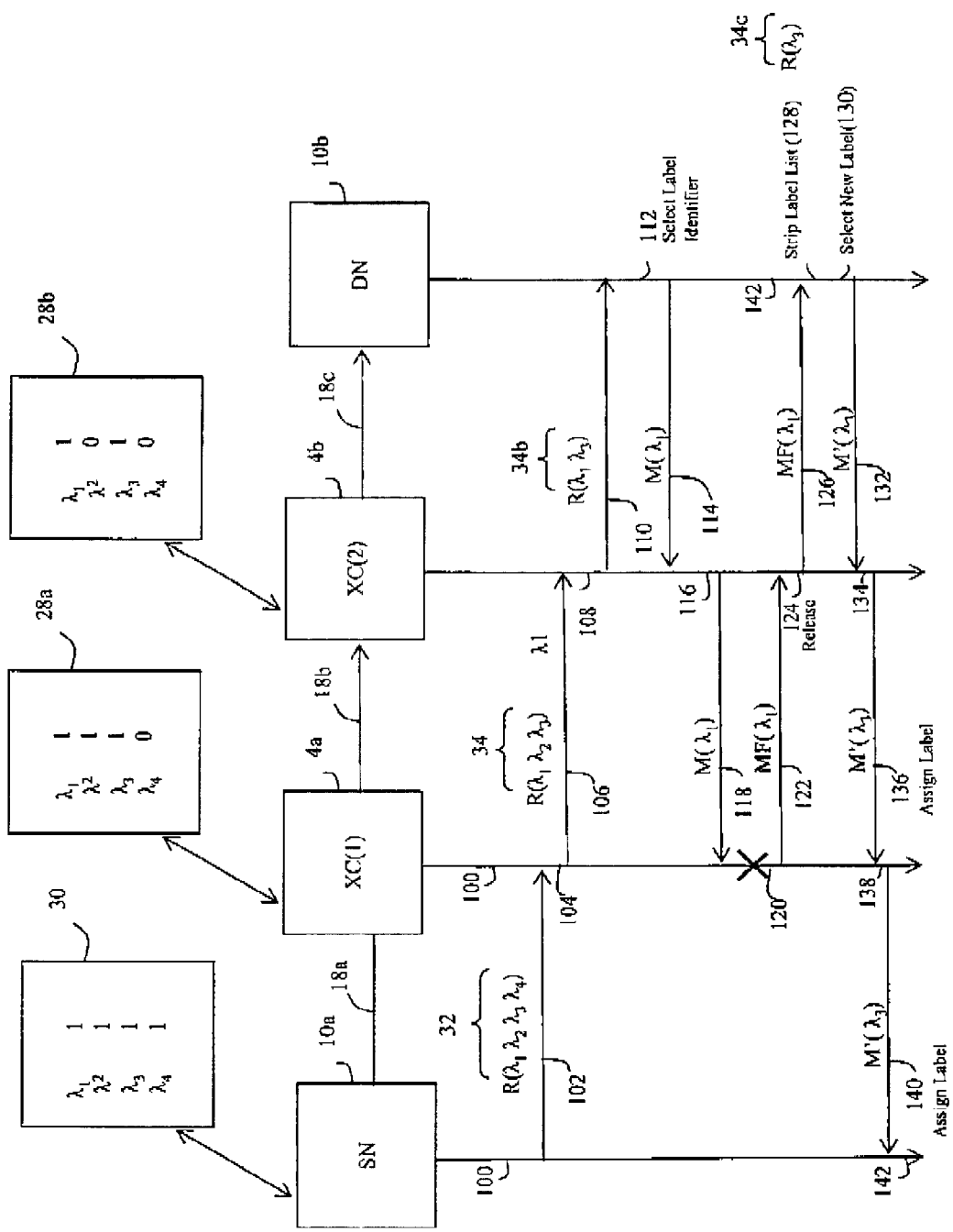
FIG. 3 is a message flow diagram schematically illustrating principal messages exchanged during the set up of an end-to-end optical path in accordance with an embodiment of the present invention.

As shown in FIG. 3, the source node 10a is provided with a respective label availability table 30 which is closely similar to that of each of the cross-connects 4a and 4b involved in the path 16. In the example illustrated in FIG. 3, the label availability table 30 of the source node 10a indicates that all possible labels ($\lambda_1$ through $\lambda_4$) are available for use on the first hop 18a of the path 16 (i.e. between the source node 10b and the first cross-connect 4a). The label availability table 28a associated with the first cross-connect 4a indicates that, of the possible labels $\lambda_1$ through $\lambda_4$, only the first three labels ($\lambda_1$ through $\lambda_3$) are available for use on the second hop 18b of the path 16 (i.e. between the first and second ross-connects 4a and 4b). Finally, the label availability table 28b associated with the second cross-connect 4b indicates that, of the possible labels $\lambda_1$ through $\lambda_4$, only the first and third labels (i.e. $\lambda_1$ and $\lambda_3$) are available for use on the third hop 18c of the path 16 (i.e. between the second cross-connect 4b and the destination node 10b).

In order to select a label and set up the end-to-end path 16, the source node 10a prepares a request message R (step 100) which includes a label list 32 identifying each of the labels which are available for use by the source node 10a for transporting LSPs over the first hop 18a of the path 16. Conveniently, the label list 32 can be prepared by extracting each label identifier from the label availability table 30 for which the associated availability flag is set to "1". The request message R including the label list 32 is then launched over a link 6 (step 102) towards the first cross-connect 4a en-route to the destination node 10b.

Upon receipt of the request message R, the first cross-connect 4a extracts the label list 32 and compares it with its associated label availability table 28a (step 104). The first cross-connect 4b performs this comparison operation by calculating the intersection between the set of labels identified in the label list 32 and the set of labels available for the next hop 18b of the path 16, as indicated by the label availability table 28a the intersection set resulting from this analysis is the set of label identifiers corresponding to labels which are available for use over the first two hops 11a, b of the path 16, this intersection set is then inserted into the request message R as a reduced label list 34, and the request message R is forwarded on to the second cross-connect 4b (step 106).

Upon receipt of the request message R including the reduced label list 34, the second cross-connect 4b extracts the reduced label list 34 and compares it with its associated label availability table 28b (step 108) in an identical manner to that described above with respect to the first cross-connect 4a. The resulting intersection set includes each label identifier corresponding to labels which are available for use over all three hops 18a–18c of the path 16. This intersection set is inserted into the request message R as a further reduced label list 34b, and forwarded to the destination node 10b (step 110).

It will be appreciated that this process of receiving the request message R; extracting the label list, and calculating the intersection e to the label list and the set of available label identifiers in an associated label availability table 28 can be repeated (over any number of hops 18) until the reduced label list is empty or the request message (containing a non-empty label list) is forwarded to the destination node 10b. At any cross-connect 4 if the reduced label list is found to be empty, then a request rejection message (not shown) can be generated and sent back to the source node 10a to indicate that no labels are available for the end-to-end path 16).

Returning now to FIG. 3, upon receipt of the request message R, the destination node 10b extracts the reduced label list 34b, and determines whether or not it contains any label identifiers (step 112). In the present example, the reduced label list 34b contains two label identifiers, namely $\lambda_1$ and $\lambda_3$. The destination node 10b then selects one of the label identifiers (e.g. by random selection), and launches a mapping message M (step 114) including the selected label identifier $\lambda_1$ back to the source node 10a, and retracing the route followed by the request message R.

As the mapping message M propagates hop-by-hop towards the source node 10a, the label corresponding to the selected label identifier $\lambda_1$ is assigned by each cross-connect 4 to the end-to-end path 16 and the corresponding entry in the respective label availability table 28 is updated. Thus in the example illustrated in FIG. 3, the mapping message M including the selected label identifier $\lambda_1$ is forwarded by the destination node 10b over the third hop 18c. Upon receipt of the mapping message M, the second cross-connect 4b extracts the selected label identifier $\lambda_1$; assigns the corresponding label to the end-to-end path 16; and updates its label availability table 28b to indicate that the label is no longer available (step 116). The mapping message M including the selected label identifier $\lambda_1$ is then forwarded over the second hop 18b to the first cross-connect 4a (step 118).

It will be appreciated that it is possible that in the period of time between reception of the request message R propagated from the source node 10a, and subsequent reception of the mapping message M propagated from the destination node 10b, a cross-connect 4 may have received another mapping message in respect of a different path and including the same label identifier. In this case, the label corresponding to the selected label identifier $\lambda$ will no longer be available, upon subsequent arrival of the mapping message M propagated from the destination node lob. This situation is illustrated in FIG. 3. Thus upon receipt of the mapping message M, the first cross-connect 4a extracts the selected label identifier $\lambda_1$ and attempt to assign the w corresponding label to the path 16. However, the corresponding label has already been assigned to another path, and is therefore no-longer available. In this circumstance, at step 120 the first cross-connect 4a prepares a mapping failure message MF including the selected label identifier $\lambda_1$ and indicating that the corresponding label is no longer available for use. The mapping failure message MF is then forwarded (steps 122–126) hop-by-hop back to the destination node 10b, so that resources already assigned to the path 16 en-route to the destination node 10b can be released.

Upon receipt of the mapping failure message MF including the selected label identifier $\lambda_1$, the destination node 10b extracts the label identifier $\lambda_1$ and strips it from the reduced label list 34b (step 128) previously received with the request message R. If the thereby stripped label list 34c is empty, then the destination node 10b forwards a request rejection message (not shown) back to the source node 10a indicating that there are no labels available for the end-to-end path 16. Otherwise, the destination node 10b selects (e.g. at random) another label identifier from the stripped label list 34c (step 130), and attempts to set up the end-to-end path 16 by launching a new mapping message M' including the newly selected label identifier toward the source node 10a and retracing the route followed by the request message R. In the present example, the stripped label list contains a single label identifier ($\lambda_3$), and this label identifier is inserted into the new mapping message M' which is launched towards the source node 10a (steps 132, 136 and 140). At each cross-connect 4, resources are assigned to the path 16 (steps 134 and 138) and the associated label availability table 28 updated. Arrival of the mapping message at the source node 10a (at step 142) including the newly selected label identifier $\lambda_3$ indicates completion of the end-to-end path 16 through the communications network 2.

Thus the present invention provides a simple means by which an end-to-end label switch path having a common label (in the present example, the label indicated by label identifier $\lambda_3$) for each hop of the path is set up. Consequently, non-agile cross-connects can participate in the end-to-end path, because it is not necessary to perform wavelength conversions between hops.

The embodiment(s) of the invention described above is(are) intended to be exemplary only. The scope of the invention is therefore intended to be limited solely by the scope of the appended claims.

I claim:

1. A method of label selection for end-to-end transport of label switched traffic through a communications network between a source node and a destination node, the method comprising the steps of:
   a) launching a request message toward the destination node from the source node, the request message including a label list having one or more label identifiers indicative of respective corresponding labels available for use by the source node; and
   b) revising the label list at each successive hop between the source node and the destination node, based on labels available for use by each respective hop, to produce a reduced label list;
   whereby the reduced label list includes any label identifiers indicative of respective corresponding labels available for end-to-end transport of label switched traffic between the source node and the destination node; and
   wherein the communications network uses wave division multiplexing (WDM) for transport of said label switched traffic, the label switched traffic made up of packets containing labels used to switch the packets between the source node and the destination node, each label comprising a respective data transport wavelength.

2. A method as claimed in claim 1, wherein the label switched traffic includes multi-protocol label switched (MPLS) traffic.

3. A method as claimed in claim 1, wherein the step of revising the label list comprises, at each successive hop toward the destination node, a step of intersecting the label list with a set of label identifiers indicative of labels available for use over the hop.

4. A method as claimed in claim 3, further comprising, at each successive hop toward the destination node, a step of sending a request rejection message to the source node if the reduced label list is empty.

5. A method as claimed in claim 1, further comprising, if the reduced label list included with the request message received by the destination node contains at least one label identifier, the step of:
   a) selecting one of the label identifiers from the reduced label list; and
   b) setting up an end-to-end label switched path between the source node and the destination node using the respective label corresponding to the selected label identifier.

6. A method as claimed in claim 5, wherein the one of the label identifiers is selected at random.

7. A method as claimed in claim 5, wherein the step of setting up an end-to-end label switched path comprises a step of sending a mapping message containing the selected label identifier from the destination node toward the source node, the mapping message retracting the path traversed by the request message.

8. A method as claimed in claim 7, further comprising, upon receipt of the mapping message at each hop, a step of assigning the label to the end-to-end label switched path if the label corresponding to the selected label identifier is still available for use by the hop.

9. A method as claimed in claim 7, further comprising, upon receipt of the mapping message at each hop, a step of sending a mapping failure message to the destination node if the label corresponding to the selected label identifier is not available for use by the hop.

10. A method as claimed in claim 9, further comprising, upon receipt of the mapping failure message by the destination node, the steps of:
    a) revising the reduced label list by removing the selected label identifier,
    b) if the reduced label list is empty, sending a request rejection message to the source node; and
    c) if the reduced label list contains at least one label identifier:
       i) selecting a new label identifier from the reduced label list; and
       ii) setting up an end-to-end label switched path between the source node and the destination node using the respective label corresponding to the selected label identifier.

11. A communications network for label selection for end-to-end transport of label switched traffic though the communications network, the communications network comprising:
    a) a source node adapted to launch a request message toward a destination node, the request message including a label list having one or more label identifiers indicative of respective corresponding labels available for use by the source node;
    b) at least one hop intermediate the source node and the destination node, each hop comprising a respective intermediate node adapted to revise the label list based on labels available for use by the respective hop, to produce a reduced label list; and
    wherein the communications network uses wave division multiplexing (WDM) for transport of label switched traffic, the label switched traffic made up of packets containing labels used to switch the packets between the source node and the destination node, each label comprising a respective data transport wavelength.

12. A communications network as claimed in claim 11, wherein the label switched traffic includes multi-protocol label switched (MPLS) traffic.

13. A communications network as claimed in claim 11, wherein each intermediate node is adapted to revise the label list by intersecting the label list with a set of label identifiers indicative of labels available for use over the respective hop.

14. A communications network as claimed in claim 13, wherein each intermediate node is further adapted to send a request rejection message to the source node if the reduced label list is empty.

15. A communications network as claimed in claim 11, wherein, upon receipt of the request message, if the reduced label list contains at least one label identifier, the destination node is adapted to:
    a) select one of the label identifier from the reduced label list; and b) set up an end-to-end label switched path between the source node and the destination node using the respective label corresponding to the selected label identifier.

16. A communications network as claimed in claim 15, wherein the destination node is adapted to set up an end-to-end label switched path by sending a mapping message containing the selected label identifier toward the source node, the mapping message retracing the path traversed by the request message.

17. A communications network as claimed in claim 16, wherein each intermediate node is responsive to reception of the mapping message to assign the label corresponding to the selected label identifier to the end-to-end label switched path if the label is still available for use by the respective hop.

18. A communications network as claimed in claim 16, wherein each intermediate node is responsive to reception of the mapping message to send a mapping failure message to the destination node if the label corresponding to the selected label identifier is not available for use by the receptive hop.

19. A communications network as claimed in claim 18, wherein the destination node is responsive to reception of the mapping failure message to:
  a) revise the reduced label list by removing the selected label identifier;
  b) if the reduced label list is empty, send a request rejection message to the source node; and
  c) if the reduced label list contains at least one label identifier:
    i) select a new label identifier from the reduced label list; and
    ii) set up an end-to-end- label switched path between the source node and the destination node using the respective label corresponding to the selected label identifier.

20. An intermediate node of a communications network adapted for end-to-end transport of label switched traffic through the communications network between a source node and a destination node, the intermediate node comprising:

a) a label availability list including label identifiers indicative of labels available for conveying label switched tic through a respective communications link connected to the intermediate node;
  b) a buffer adapted to receive a request message propagated through the communications network from the source node, the request message including a label list having label identifiers indicative of labels available for conveying label switched traffic between the source node and the intermediate node;
  c) a processor adapted to revise the label list included in the received request message, based on the label availability list, to produce a reduced label list; and
  wherein the communications network uses wave division multiplexing (WDM) for transport of label switched traffic, the label switched traffic made up of packets containing labels used to switch the packets between the source node and the destination node, each label comprising a respective data transport wavelength.

21. An intermediate node as claimed in claim 20, wherein the processor is adapted to revise the label list by intersecting the label list with the label availability list.

22. An intermediate node as claimed in claim 20, further comprising means for assigning a label to an end-to-end path between the source node and the destination node in response to a mapping message received from the destination node, the mapping message containing a label identifier corresponding to the label.

23. An intermediate node as claimed in claim 20, further comprising means for sending a mapping failure message to the destination node in response to a mapping message received from the destination node containing a label identifier corresponding to a label that is not available for converting label switched traffic.

24. An intermediate node as claimed in claim 20, further comprising means for sending a request rejection message to the source node if the reduced label list is empty.

* * * * *